United States Patent [19]

Novinson

[11] Patent Number: 4,527,062
[45] Date of Patent: Jul. 2, 1985

[54] PORTABLE INFRARED SPECTROPHOTOMETER

[75] Inventor: Thomas Novinson, Ventura, Calif.

[73] Assignee: The United States of America as represented by the Secretary of the Navy, Washington, D.C.

[21] Appl. No.: 510,851

[22] Filed: Jul. 5, 1983

[51] Int. Cl.³ ............................................. G01N 21/35
[52] U.S. Cl. ................................................. 250/351
[58] Field of Search ............................ 250/351, 370 J

[56] References Cited

U.S. PATENT DOCUMENTS

| | | | |
|---|---|---|---|
| 3,091,690 | 5/1963 | McHenry | 250/339 |
| 3,332,315 | 7/1967 | Wilks, Jr. | 356/319 |
| 3,471,698 | 10/1969 | Mausteller | 250/351 |
| 3,524,983 | 8/1970 | Voelz | 250/341 |
| 3,582,209 | 6/1971 | La Rosa et al. | 356/51 |
| 3,669,545 | 6/1972 | Gilby | 356/320 |
| 3,902,807 | 9/1975 | Fleming et al. | 356/300 |
| 4,169,676 | 10/1979 | Kaiser | 356/39 |
| 4,303,859 | 12/1981 | McCue | 250/338 |

FOREIGN PATENT DOCUMENTS 2030323 1/1971 Fed. Rep. of Germany .

OTHER PUBLICATIONS

P. S. Kireev et al., "Fast Radiation Detectors Using Photoresistive $Cd_xHg_{1-x}Te$", *Soviet Physics-Doklady*, vol. 15, No. 8, (Feb. 1971), pp. 755-757.

*Primary Examiner*—Alfred E. Smith
*Assistant Examiner*—Constantine Hannaher
*Attorney, Agent, or Firm*—Robert F. Beers; Joseph M. St. Amand; Thomas M. Phillips

[57] ABSTRACT

A portable infrared spectrophotometer for nondestructive testing of coatings, plastics, rubber and other organic construction materials. A single source of infrared light is formed into two beams. One beam is directed to the surface of a sample where it is reflected off the surface of the sample at least four times. The other beam follows a similar path but bounces off a neutral surface. The two beams are combined and focused onto a detector. The output of the detector is proportional to the energy absorbed by the surface of the test sample. A pen recorder is used to provide a graphic display of the spectrum generated.

1 Claim, 1 Drawing Figure

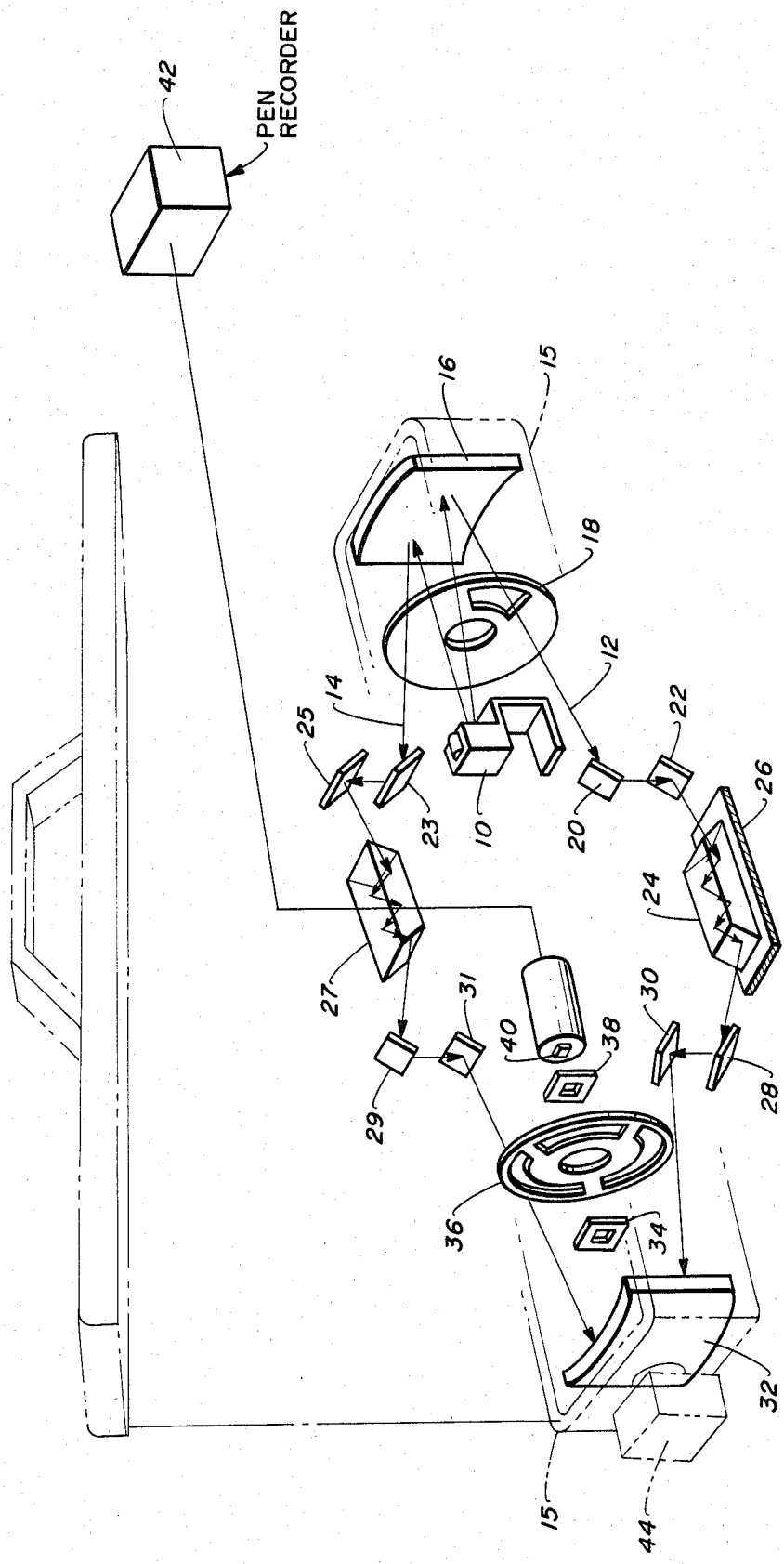

4,527,062

PORTABLE INFRARED SPECTROPHOTOMETER

BACKGROUND OF THE INVENTION

The present invention relates to spectroscopy and more particularly to infrared reflectance spectroscopy.

Naval architects and engineers often require immediate information on identity or composition of materials especially when located in remote areas. The acquisition of laboratory results from a remote location is time consuming and costly. Removal of samples by scraping dry paint off concrete or metal, cutting tarpaper roofing, etc., for shipment to the laboratory for testing is time consuming and costly. The removal of the samples for shipment may result in contamination or destruction of the sample and poor data as well as damage to the structure itself. A portable analytical instrument for nondestructive analysis of coatings, plastics, rubbers and other organic construction materials is desired. There are no known portable instruments for performing the above-desired test.

SUMMARY OF THE INVENTION

The present invention provides for a portable infrared spectrophotometer capable of nondestructively analyzing a solid sample of organic material to qualitatively identify and distinguish it from all other materials. A single source of infrared light is used to generate two infrared light beams of equivalent energy and optical path lengths. The function of the first beam is to nondestructively interact with the sample surface to provide selective light absorption in the region of 2.0 to 15.0 microns (infrared). The function of the second beam is to cancel the spurious information interjected by absorbance arising from gases in air which absorb infrared light. When the two beams are recombined, passed through a circular variable filter and detected, a spectrum of wavelength (energy) vs. percent transmission as a series of uniquely identifying spectral peaks are provided to identify that specific material.

OBJECTS OF THE INVENTION

Accordingly, an object of the invention is the provision of a portable infrared spectrophotometer for the identification of solid organic samples.

Other objects, advantages and novel features of the invention will become apparent from the following detailed description of the invention when considered in conjunction with the accompanying drawings wherein:

BRIEF DESCRIPTION OF THE DRAWING

There is shown in the single FIGURE a schematic diagram of the apparatus with the necessary function to provide the desired results.

DESCRIPTION OF THE PREFERRED EMBODIMENT

Referring now to the single FIGURE wherein there is shown a single source of infrared light 10 formed into a first infrared beam 12 and a second or reference infrared beam 14 by means of a parabolic mirror 16. Each of the beams are interrupted by a chopper disc 18. Beam 12 is directed by mirrors 20 and 22 onto prism 24. Prism 24 is positioned with respect to the instrument housing 15 so that the larger surface of prism 24 may be pressed against the surface of a sample 26 being investigated. Beam 12 enters prism 24 and is reflected off the sample 26 surface several times (at least 4) and then exits and is redirected by mirrors 28 and 30 to its original direction. At the same time reference beam 12 is directed by mirrors 23 and 25 to prism 27 where it is reflected without absorption and redirected by mirror 29 and 31 to its original path.

Parabolic mirror 32 intercepts the two beams and converges them into a single beam. The converging light passes through slit 34, continuous filter 36 and a second slit 38 and converges on the front of detector element 40. Filter 36 is available commercially from Optical Coating Laboratory, Inc., Santa Rosa, Calif. and comprises three segments. Segment one is made of quartz and allows light to pass from 2.5 μm to 4.5 μm. Segment two has a germanium band pass element and an Irtran I blocking element and allows light to pass from 4.4 μm to 8.0 μm. Segment three has a germanium band pass element and allows light to pass from 7.9 μm to 14.5 μm. Detector element 40 is a mercury cadmium telluride (HgCdTe) crystal mounted in a Hughes Corp. Probeye dewar which is cooled to 70 kelvin (K.) by means of a demand flow cryostat using argon gas available commercially from Santa Barbara Research Corp., Goleta, Calif. The output of detector 40 is fed to pen recorder 42 where a spectrum or fingerprint of the sample 26 is generated.

Prisms 26 and 27 are substantially flat, symmetrical trapezium in plan with inclined end faces at which the infrared beam enters and leaves, and two parallel faces which form the guides for the internal reflection of the beam. Prisms 26 and 27 are made of thallium bromoiodide also called KRS-5.

The function of circular variable filter 36 is to convert the polychromatic infrared light into monochromatic infrared energy to produce a spectrum of wavelength vs. transmittance.

Obviously many modifications and variations of the present invention are possible in light of the above teachings. It is therefore to be understood that within the scope of the appended claims the invention may be practiced otherwise than as specifically described.

What is claimed is:

1. A portable infrared spectrophotometer for the nondestructive testing and identification of solid organic samples such as plastics, rubber and other organic construction materials, the combination comprising:
   a. a source of polychromatic infrared energy in the range of 2–15 microns;
   b. means for forming energy from said infrared source into two infrared beams of equivalent optical lengths;
   c. means for deflecting one of said infrared beams onto the surface of a sample to be identified;
   d. means for reflecting said beam off said sample surface a predetermined number of times;
   e. means for deflecting said beam back into its original path;
   f. a continuous filter for converting the polychromatic infrared light into monochromatic infrared energy to produce a spectrum of wavelength vs. transmittance;
   g. means for recovering said converted beam and converging said reflected beam along with said other beam to impinge on a single detector to generate a signal proportional to the infrared energy absorbed by said sample;
   h. said signal being used to drive a pen on a chart recorder.

* * * * *